United States Patent [19]
Michael

[11] Patent Number: 5,569,033
[45] Date of Patent: Oct. 29, 1996

[54] PINNED DENTAL MODELS AND THEIR PREPARATION AND USE

[76] Inventor: Robert M. Michael, 25 Devonshire Dr., Westampton, N.J. 08060

[21] Appl. No.: 311,521

[22] Filed: Sep. 23, 1994

[51] Int. Cl.⁶ .......................... A61C 19/00; A61C 11/00
[52] U.S. Cl. ................................. 433/74; 433/213
[58] Field of Search ........................ 433/74, 213, 60, 433/54

[56] References Cited

U.S. PATENT DOCUMENTS

| | | | |
|---|---|---|---|
| 2,042,200 | 5/1936 | Torp | 433/213 |
| 3,498,580 | 3/1970 | Wilson | 433/74 |
| 3,521,354 | 7/1970 | Stern et al. | 433/74 |
| 3,553,839 | 9/1969 | Gores | 433/74 |
| 3,896,548 | 7/1975 | Zahn | 433/74 |
| 3,932,939 | 1/1976 | Weissman | 433/213 |
| 4,129,281 | 12/1978 | Cooper | 433/74 |
| 4,840,565 | 6/1989 | Poveromo | 433/74 |

Primary Examiner—Cary E. O'Connor

[57] ABSTRACT

A dental model for use with or without articulating devices, wherein the model has a front face and a rear face, at least one dowel pin affixed to the model and having a free end positioned outwardly from the rear face, a recess form nut having a bore which frictionally receives the free end, a support of rigid material having a proximal surface and a distal surface and positioned with the rear face of the model and the proximal surface of the support juxtaposed, the dowel pin with the form nut thereon removably extending through the support to position the free end adjacent the distal surface of the support, at least an outer portion of the form nut being exposed to view from the distal side of the support, and a shoulder on the outer portion of the form nut adapted for contact with a removal tool for removing the form nut from the dowel pin to leave the free end exposed through the distal side of the support whereby the free end becomes readily accessible for contact with an extraction tool for forcing the dowel pin inwardly of the distal surface of the support for removing the dowel pin and the die model from the support.

21 Claims, 3 Drawing Sheets

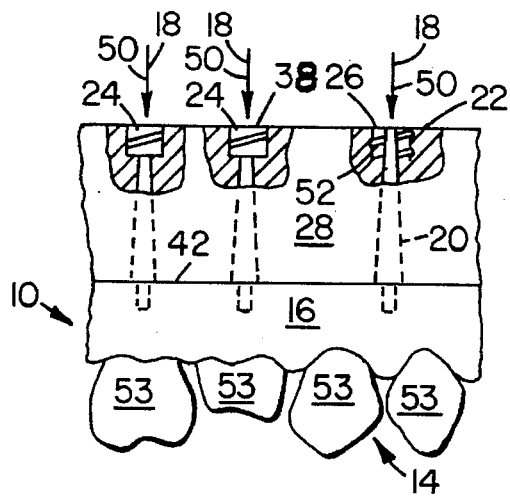
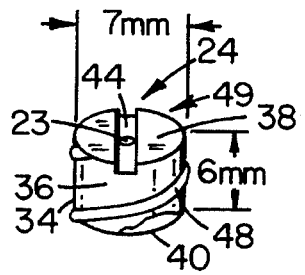
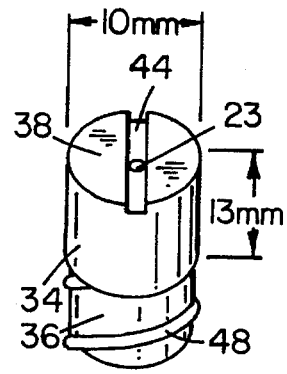
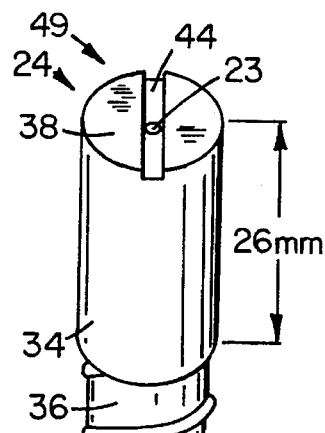
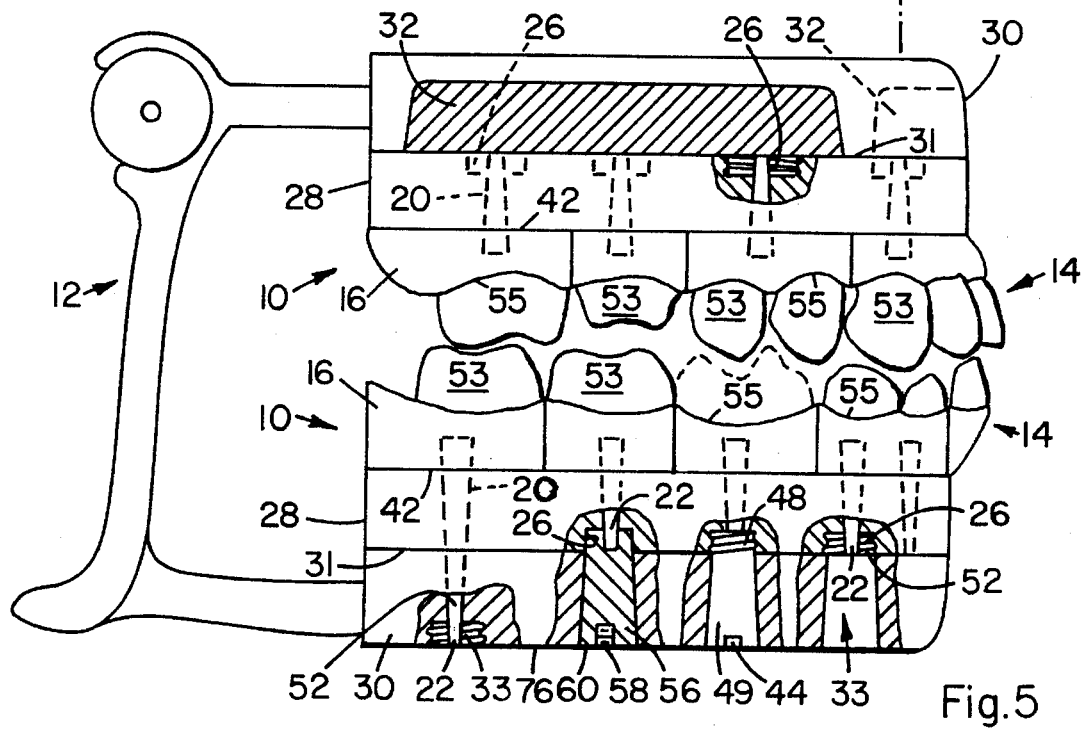

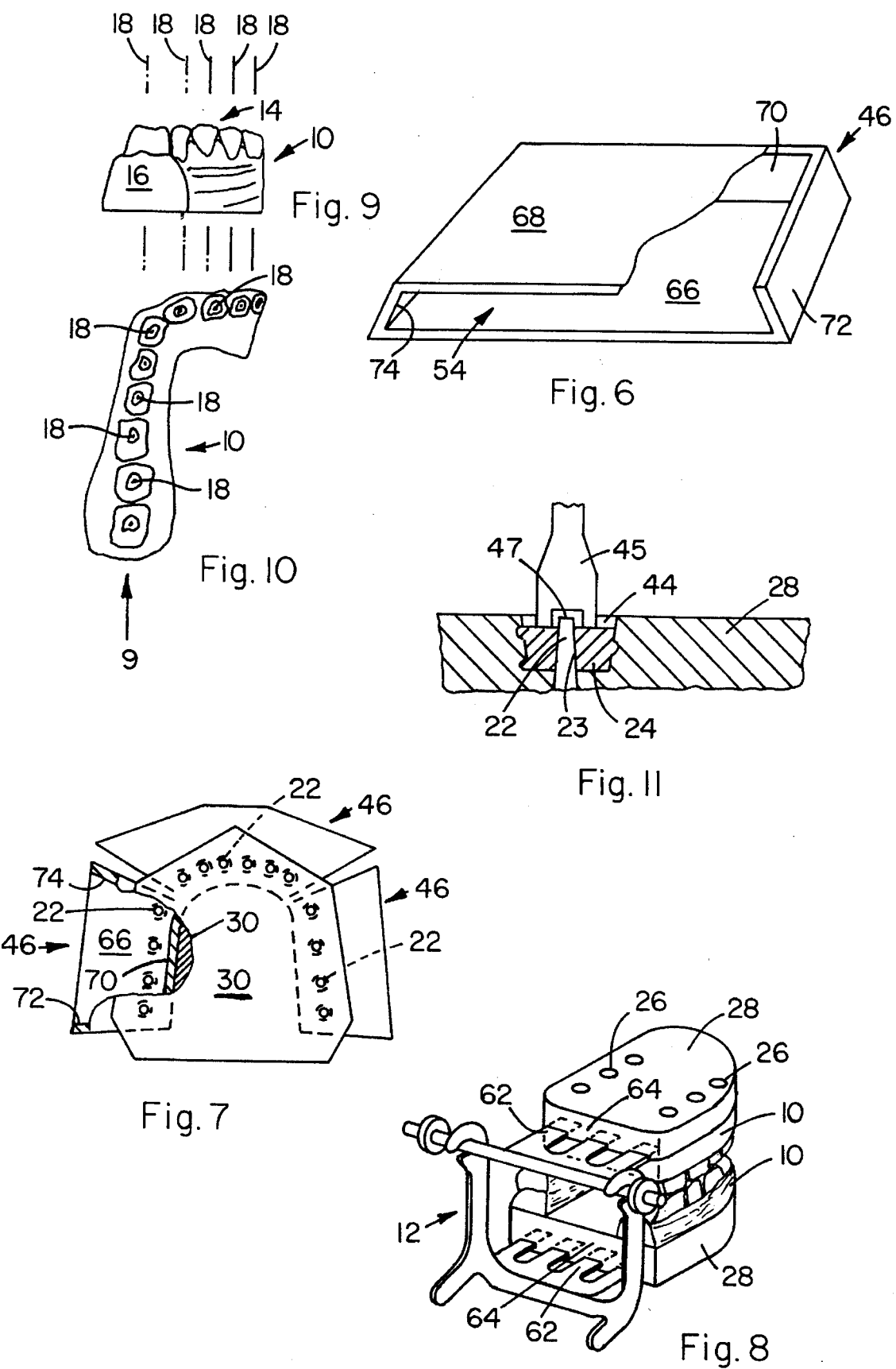

PINNED DENTAL MODELS AND THEIR PREPARATION AND USE

BACKGROUND OF THE INVENTION

1. Field of the Invention

This invention concerns uniquely pinned dental die models, i.e., positive moldings of teeth and associated gum area, and their preparation and use, and particularly concerns the means and method for providing easy and convenient access to the free ends of the conventionally employed locator dowel pins for selective removal of segments of the cut die model with their associated dowel pins affixed thereto.

2. Description of the Prior Art

In the field of tooth or plate reconstruction, die models of teeth and associated gum portions are typically employed for making the prosthodontic appliances such as bridgework, crowns, plates, individual teeth and the like. This is done by forming an impression mold out of a quick-setting impression material such as plaster of paris around the actual teeth and associated gum portions or areas of the patient which duplicates as a negative molding or impression the patient's teeth and gum portions. Thereafter, the negative molding of the teeth and gum portions is converted to a positive molding from the impression, which positive molding or die model is then utilized in the construction of the dental prosthesis.

In a typical conventionally used procedure, as depicted in FIGS. 12 and 13, after molding of the die model 11, the posterior face 13 of the reproduced gum portions or base 15 is sanded flat and several dowel pins 17, typically made of brass, are inserted into holes 19 drilled into the die model base from said posterior face and adhesively secured therein. Typically at least one hole and pin are employed for each segment 21 to be cut from the die model.

To facilitate the cutting of the die model into said segments and for providing a support 25 from which and upon which the segments can be removed and replaced respectively in proper relative positions, it is conventional that prior to cutting, the die model is positioned over the support 25 comprising a mass of partially cured material such as plaster of paris positioned on a flat surface 27 and which is approximately the consistency of dough. The dowel pins are then forced into the dough-like material of the base support at its proximal surface 29 such that the posterior face 13 of the die model base comes to rest on the proximal surface 29 of the support of partially cured material. The posterior face 13 of the die model base is generally treated with a separating medium or releasing agent to prevent adhesion to the support during the cure of the support. Material is then allowed to harden around the pins, after which the posterior surface 35 thereof is ground or otherwise formed into an appropriate configuration for being received e.g., by an adaptor member such as 39 shown in dotted line, of an articulator, e.g., a configuration roughly of the lateral dimensions and shape of the die model, for duplication of jaw action as the dental prosthesis subsequently is shaped in accordance with the die model.

After hardening of the support material, the die model, while still pinned to the, support by means of the sockets 41 formed in the support can be cut into various separate segments 21 as desired. The individual segments, each carrying one or more dowel pins, are then selectively removed from the support and from the rest of the die model and positioned in work apparatus or hand-held for further forming operations. Thereafter, the segment may be replaced in proper position on the support and retained thereon by the said one or more dowel pins which are reinserted into their sockets which were formed in the support material upon curing. The pins thus precisely reposition the separate segments relative to the rest of the die model.

With reference to the above description of prior practices, a tedious and time consuming problem exists, with respect to preparing the combination of (1) die model, i.e., positive die stone replication of teeth and associated gum areas and having dowel pins affixed thereto, and (2) a support to which the die model is removably affixed by said dowel pins being inserted into the sockets formed in the support. The problem arises from the fact that the dowel pins are first positioned in the uncured base material which is then hardened around the pins. This process gives a significant frictional or adhesive attachment of the support to the pins and requires that the free ends 43 of the pins be accessible from the posterior surface 35 of the support such that force can be applied to said free ends in order to drive the pins out of their sockets and separate the entire die model or segments thereof from the support.

Heretofore, the technique of choice for exposing the free ends of the pins has been to chip or cut away the areas 51 of said support shown in dotted line in FIG. 13, at its posterior surface 35 immediately surrounding said free ends in order to expose sufficient portions of said free ends to allow engagement thereof with an impact or other force providing tool to drive the pins from their sockets. This chipping or cutting is laborious, tedious and time consuming, and produces a product of crude and displeasing appearance. Also employed is the technique of molding the support material around the pins such that the free ends thereof extend outwardly from the posterior surface of the support and are thus automatically exposed. This construction however, in many situations, cannot be used, such as where the support itself must sit flat on a surface of an articulator casting or adaptor member such as 39 or other foundation means.

Exemplary of the prior art which discloses such use of locator dowel pins and a supporting structure for the die model segments are the following U.S. Pat. Nos.: 4,398,884; 3,937,773; 4,078,310; 4,265,619; 4,721,464; and 4,917,347, the general disclosures of which regarding articulators, casting materials, and dental models and their use are hereby incorporated herein by reference.

OBJECTS OF THE INVENTION

Objects therefore of the present invention are: to provide a dental die model having locator dowel pins affixed thereto wherein the free ends of the pins are readily accessible from the posterior surface of a support, which supports said model, and to provide a unique method for forming such die model; to provide such a model and support for use in articulating means having die model/support adapter support castings which are modified to provide access to said free ends even when said support is permanently affixed to said adaptor to provide means and methods for so modifying said adapters to provide highly accessible side or top access ports for contacting said free ends; and to provide all of the above structures and methods in simple and inexpensive forms.

SUMMARY OF THE INVENTION

The above and other objects hereinafter becoming evident have been attained in accordance with the present invention which is defined in its preferred broad structural and method embodiments as expressed below.

I. A dental die model for use with or without articulating devices, said model having a tooth side and a generally axially opposed base which are oriented generally along a bite axis, at least one dowel pin being affixed to said model and having a free end extending outwardly from said base generally along said bite axis, and from recess form means fictionally mounted on said free end and adapted to form a recess in a support of casting material encasing said pin and from recess form, said recess appearing upon removal of said recess form from said free end and said support and thereby exposing said free end lying within said recess.

II. Articulator means having adaptor means for mounting the support of I above on said articulator means, wherein said adaptor means is provided with access port means for allowing said free ends to be readily contacted with force applying tool means for separating said entire die model or segments thereof from said support.

III. The method for constructing the combination of a dental die model and a support therefor, comprising forming a die model from a negative impression of a tooth area including gum portions within said area, said model having a tooth side and a generally opposite base, mounting at least one dowel pin on said base and extending outwardly therefrom, said pin terminating in a free end, mounting a recess form means on said free end, said form means having a body with side surface portions and end surface portions, forming a support onto said base and surrounding said at least one pin and said recess form means but leaving said end surface portions exposed, said model being readily separable from said support at the juncture thereof, said end surface portions having form removal assisting means thereon, and contacting said removal assisting means with removal means and removing said recess form means from said free end and said support to thereby leave said free end exposed within the thus formed recess.

IV. The method for constructing articulator means having adaptor means for mounting a support of a die model-support combination on said articulator means, wherein said adaptor means is provided with access port means for allowing the free end of at least one dowel pin extending through said support to be readily contacted with force applying tool means for separating said entire die model or a segment thereof from said support, said method comprising mounting access port form means on either said free end or on said support and covering said free end therewith, forming said adaptor means onto said support and around said access port form, and removing said access port form from said adaptor means to thereby leave said free end exposed and readily contactable by force applying means to push said at least one pin out of said support.

In certain preferred embodiments:

(a) said recess form means comprises a body means of generally round shaft configuration which is provided with screw thread means on its outer surface, said body means having an axis of rotation whereby said body means can be readily backed out of said support by rotation thereof about its axis of rotation to thereby leave said free end exposed for contact through said support;

(b) said body means having shoulder means on its outer end for contact with tool means for rotating said body means;

(c) said access port means is formed either in the side of said adaptor means or generally axially therethrough.

BRIEF DESCRIPTION OF THE DRAWINGS

The invention, in certain preferred embodiments thereof, is shown in the accompanying drawings and explained the following description thereof, wherein:

FIG. 1 is a side elevational view, partially sectioned, of a dental die model with dowel pins affixed thereto and with recess forms frictionally mounted on the free ends of the pins, and with a east support surrounding and imbedding said pins and recess forms;

FIGS. 2, 3 and 4 are perspective views of three sizes of a preferred recess form with typical dimensions shown;

FIG. 5 is an enlarged partially sectioned side view of an articulator having an upper and lower stone die model including the supports therefor, said supports being mounted on the adaptor castings (plaster) of an articulator, and showing various embodiments and stages in the use of the pins and recess formers;

FIG. 6 is an enlarged perspective view of a form employed to make the side access port in the top adaptor casting of FIG. 5 with a portion of the top broken away;

FIG. 7 is a top view of the top adaptor casting or plaster of FIG. 5 showing useful positioning on three sides thereof of the side access port forms during casting of the upper adaptor casting for allowing side access to the free ends of the die dowel pins, the top of one of which forms is broken away for clarity;

FIG. 8 is a perspective view of the stone die model supports themselves mounted directly on the arms or blades of an articulator;

FIG. 9 is an end view taken in the direction of arrow 9 in FIG. 10, of a typical die model showing the substantial vertical orientation of the bite axis;

FIG. 10 is a top view of the model of FIG. 9 showing the bite axis of several tooth positives end on;

FIG. 11 is an exemplary notched screw driver blade in position in a slot 44 in the top of form 24, which blade can be conveniently used to remove the recess or access port forms.

DESCRIPTION OF THE PREFERRED EMBODIMENTS

Figure 13:
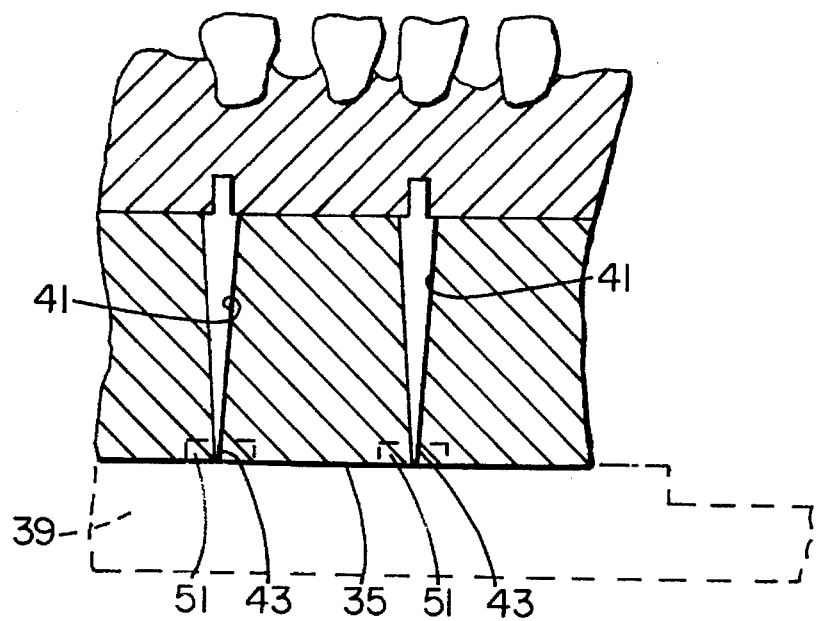
Figure 12:
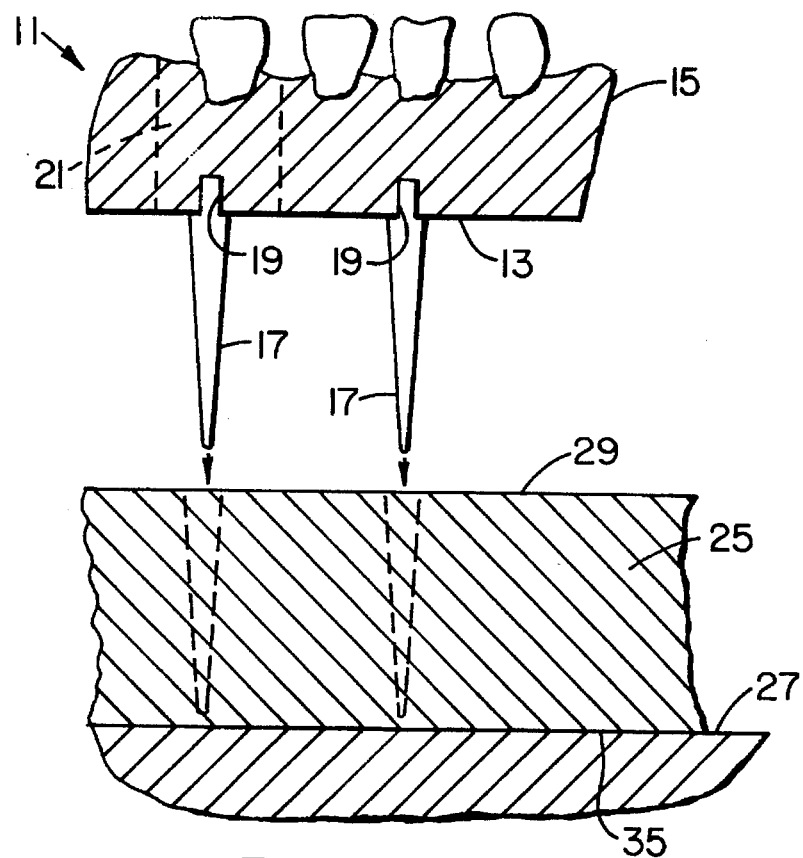

Referring to the FIGS. 1–11 of drawings and with particular reference to the claims hereof and embodiment I set forth above, the present invention is described as a dental die model 10 for use with or without articulating devices 12, said model having a tooth side 14 having one or more tooth positive mold and a generally axially opposed base 16 which are oriented generally along bite axes 18, said moldings 53 lying adjacent the proximal surfaces 55 of said base 16, at least one dowel pin 20 being affixed to said model and having a free end 22 extending outwardly from said base generally along said bite axis, and recess form means 24 fictionally mounted on said free end 22 which protrudes through aperture 23 axially formed through form 24, said form being adapted to form a recess 26 in a support 28 of casting material encasing said pin and recess form means 24, said recess 26 appearing upon removal of said recess form means from said free end and from said support and thereby exposing said free end 22 lying within said recess 26. The terms "bite axis" employed herein include the multiple axes 18 shown in FIG. 1 and any such axes which are substantially parallel thereto.

With reference to embodiment II set forth above, the invention comprises articulator means 12 having adaptor means 30 for mounting the support 28 of I above on said articulator means 12, wherein said adaptor means 30 is provided with access port means 32 for allowing said :free ends 22 to be readily contacted with force applying tool means for separating said entire die model 10 or segments thereof from said support 28.

With reference to embodiment set forth above, a preferred method for constructing the combination of a dental die model 10 and a support 28 therefor, comprises forming said die model 10 from a negative impression of a tooth area including gum portions within said area, said model having a tooth side 14 and a generally axially opposite base 16, mounting at least one dowel pin 20 on said base 16 and extending outwardly therefrom, said pin terminating in a free end 22, mounting a recess form means 24 on said free end 22, said form means 24 having a body 34 with side surface portions 36 and outer and inner end surface portions 38, 40 respectively, forming said support 28 onto said base 16 and surrounding said pin 20 and said recess form means 24 but leaving said outer end surface 38 portions exposed, said model 10 being readily separable from said support 28 at the juncture 42 thereof, said outer end surface portion 38 having removal assisting means such as screw driver slot 44 thereon, and contacting said removal assisting means with removal means such as a notched screw driver blade 45 as shown in FIG. 11, and removing said recess form means 24 from said free end 22 and said support 28 to thereby leave said free end 22 exposed within the recess 26 thus formed.

With reference to embodiment IV set forth above, a preferred method is described for constructing articulator means having adaptor means for mounting a support of a die model/support combination on said articulator means, wherein said adaptor means 30 is provided with side access port means 32 of any desired configuration for allowing the free end 22 of a dowel pin 20 extending through said support 28 to be readily contacted with force applying tool means for separating said entire die model or a segment thereof from said support 28, said method comprising mounting side access port form means 46 on either said free end 22 or on said support 28 and covering said free end 22 therewith, forming said adaptor means 30 onto the distal surface 31 of said support 28 and around said side access port form means 46 or said axial access port form means 49, and removing said access port form means from said adaptor means to thereby leave said free end exposed and readily contactable by force applying means to push said pin out of said support.

In further detail, the recess form means 24 comprises a body means 34 of generally round shaft configuration, the side surface portions 36 of which are provided with screw thread means 48, said body means having an axis of rotation 50 whereby said body means can be readily backed out of said support by rotation thereof about said axis of rotation to thereby leave said free end 22 exposed for contact through said support. For this purpose, said body means is provided with shoulder means such as slot 44 on its outer surface portions 38 for contact with tool means such as a screw driver blade 45 for rotating said form means. The body 34 is preferably tapered to allow it to be more easily removed from the support. This form means can be of metal, plastic, ceramic or other rigid and durable material.

With reference to FIG. 5, one of the dowel pins 52 is shown as being sufficiently long to extend all the way through the support 28 and through the plaster 30 of the articulator adaptor member 30 whereby the axial access port 33 formed in the plaster receives the free end 22 of the pin. In this variation, the support 28 is first cast around the pin with the pin protruding from the distal surface 31 of said support. For this variation, the short access form means shown in FIG. 2 will suffice. It is noted that in the use of this screw type of form means, whether for making the recesses 26 or the axial access port means 33, the thread means 48 on the form means are encased in the casting material, i.e., plaster of paris or die stone, and thereby forms the mating thread means 52 in said material which provides the outward vector forces upon rotation of the form means to back it out of the casting material.

It is seen from FIG. 11 that blade 45 is preferably notched at 47 to allow the free end 22 of the dowel pin to extend all the way to the outer surface of either the support 28 or the plaster 30 for allowing ready access to said free end.

In FIG. 5 a further variation in axial access port form means or recess form means construction is shown at 56 wherein threads are not provided on its inner or proximal end, but rather a threaded bore 58 is formed in its outer or distal end 60 for threadedly receiving a screw or bolt, the head of which can be gripped and pulled or rotated, or struck outwardly to dislodge the form to expose free end 22. It is particularly noted, that if desired for some special purpose, a form such as 49 or 56 may be dimensioned to extend significantly beyond the outer or distal surface 76 of he plaster such that it can be gripped by any means to remove the form and thus expose he free end of the pin.

Referring to FIGS. 5, 6 and 7, the side access port means 32 are formed around port forms 46 which are of flexible material, e.g., PVC or polyolefin elastomer, and formed with a hollow cavity 54 such that after the casting of the plaster, the form can easily be pulled therefrom by virtue of the compressibility and deformability of the elastomeric floor 66, top 68, rear wall 70, and side walls 72, 74 of the form. This removal of the forms will leave the free ends 22 exposed as shown in the upper die model of FIG. 5. A screw driver type of tool having a right angle bend at its end can be easily inserted into port means 32 to press the pin out of support 28.

Referring to the variation shown in FIG. 8, the die models 10 are affixed to their supports 28 into which the blades 62 of an articulator are imbedded at the rear edges 64 of the support during the casting of the supports, or adhesively secured in grooves previously provided through the rear edges of the supports.

The invention has been described in detail with particular reference to preferred embodiments thereof, but it will be understood that variations and modifications will be effected with the spirit and scope of the invention.

I claim:

1. A dental die model for use with or without articulating devices, said model having a tooth side containing at least one tooth positive molding affixed to a proximal surface of a base, said model having a bite axis, said tooth side and base being oriented generally along said bite axis, at least one dowel pin affixed to said model and having a free end extending outwardly from a distal surface of said base generally along said bite axis, and recess form means fictionally mounted on said free end and adapted to form access in a distal surface of a support of cured casting material encasing said pin and recess form means, said form means having side surface means provided with threads and an outer end surface portion, said threads being adapted to form mating threads in said support during casting thereof whereby when said form means is engaged by a tool and rotated, said form is screwed out of said recess against the strength of the bond between the cured casting material and said form means such that said recess becomes exposed upon removal of said form means from said free end and from said support which thereby exposes said free end of said pin lying within said recess.

2. The model of claim 1 wherein said recess form means comprises a body means of generally round cross-sectional configuration which a high-pitch is provided with screw thread of less than two revolutions circumferentially around said body means; on its outer surface, said body means having an axis of rotation whereby said body means can be and rapidly backed out of said support by rotation thereof about said axis to thereby leave said free end exposed for contact through said support.

3. The model of claim 2 wherein said body means has shoulder means on its outer end for contact with tool means for rotating said body means.

4. The model of claim 1 wherein said side surface means is tapered radially outwardly toward said outer end surface to facilitate breaking of said bond.

5. The method for constructing the combination of a dental die model and a support therefor, comprising forming a die model from a negative impression of a tooth area including gum portions within said area, said model having a tooth side and a generally opposite base, mounting at least one dowel pin on said base and extending outwardly therefrom, said pin terminating in a free end, mounting a recess form means on said free end, form means having a body with side surface portions and end surface portions, forming a support onto said base and surrounding said pin and recess form means but leaving said end surface portions exposed, said model being readily separable from said support at the juncture thereof, said end surface portions having removal assisting means thereon, and contacting said removal assisting means with removal means and removing said recess form means from said free end and said support to thereby leave said free end exposed within the thus formed recess.

6. The method for constructing articulator means with adaptor means mounting a die model-support combination on said articulator means, wherein said die model-support combination comprises a die model having a tooth side containing at least one tooth positive molding affixed to a proximal surface of a base and having a bite axis, said tooth side and base being oriented generally along said bite axis, at least one dowel pin being affixed to said model and having a free end extending outwardly from a distal surface of said base generally along said bite axis, and a support of cured casting material encasing said pin wherein as a result of the casting of said support a recess is formed in a distal surface thereof and said free end of said pin lies in said recess, wherein said adaptor means is provided with access port means for allowing said free end of said, dowel pin to be readily contacted with force applying tool means for separating said entire die model or a segment thereof from said support, said method comprising mounting access port form means on said distal surface of said support and covering said recess and free end therewith, forming said adaptor means of casting material onto said distal surface of said support and around said access port form and curing the same, and removing said access port form from said adaptor means to thereby leave said recess and free end exposed such that said free end is readily contactable by force applying means to push said pin out of said support.

7. The method of claim 6 wherein said access port means is formed either through the side of said adaptor means or generally axially therethrough.

8. The method of claim 6 wherein said access port form is of compressible material and extends outwardly to the side of said support whereby after said adapter means is formed, said form can be pulled outwardly away from said support and adapter means to leave a side access port for accessing said free end of said pin.

9. The method of claim 6 wherein said port form means has a distal end surface having shoulder means thereon for being engaged by a tool for breaking the bond between said port form means and said adaptor means for removing said port form means from said adaptor means and thereby exposing said free end.

10. The method of claim 9 wherein an inner proximal end of said port form means is provided with threads which mate with threads which were formed in a wall of said recess during casting of said support, whereby said port form means can be screwed out of said support.

11. A dental model for use with or without articulating devices, comprising a die model having a front face and a rear face, at least one dowel pin affixed thereto and having a free end positioned outwardly from said rear face, a recess form nut means having a bore which frictionally receives said free end, support means of rigid material having a proximal surface and a distal surface and positioned with said rear face of said die model and said proximal surface of said support means being juxtaposed, said dowel pin with said form nut means thereon removably extending through said support means to position said free end adjacent said distal surface of said support means, at least an outer portion of said form nut means being exposed to view from the distal side of said support means, and shoulder means on said portion of said form nut means adapted for contact with a removal tool for removing said form nut means from said dowel pin to leave said free end exposed through said distal side of said support means whereby said free end becomes readily accessible for contact with an extraction tool for forcing said dowel pin inwardly of said distal surface of said support means for removing said dowel pin and said die model from said support means.

12. The dental model of claim 11 wherein said nut means is provided with screw thread means on its outer surface such as to form mating thread means daring the casting thereof in the adjacent portions of said support means.

13. A combination of dental die model and articulating device, said model having a tooth side containing at least one tooth positive molding affixed to a base and having a bite axis, said tooth side and base being oriented generally along said bite axis, at least one dowel pin affixed to said model and having a free end extending outwardly from said base generally along said bite axis, a support of cured casting material encasing said pin and having a distal surface, recess means in said distal surface, said free end extending into and lying within said recess means, said articulating device having adaptor means on which said support is mounted with its said distal surface of said support in contact with said adaptor means, wherein said adaptor means is provided with access port means thru which said free end lying within said recess means can be contacted with force applying tool means for pushing said pin out of said support and separating the entire die model or segments cut therefrom from said support.

14. The combination of claim 13 wherein said end surface portion is provided with slot means extending across said end surface portion.

15. The method for constructing a combination of a tooth die model and an articulating device comprising providing a tooth die model having a tooth side containing at least one tooth positive molding affixed to a proximal surface of a base and having a bite axis, said tooth side and base being oriented generally along said bite axis, affixing at least one dowel pin to said base, said pin having a free end extending outwardly from a distal surface of said base generally along said bite axis, frictionally mounting recess form means on said free end, said form means having an outer end surface portion with shoulder means formed thereon, casting a support of casting material around and encasing said pin, said form means and a portion of an arm of said articulating device whereby as a result of the casting of said support a distal surface thereof and said end surface portion of said form means lie substantially in a common exposed plane, said form means having side surface threads which have formed mating threads in said support during casting thereof, and engaging said shoulder means with a removal tool and screwing said form out of said support against the strength of the bond between the cured casting material and said form to provide a recess in said distal surface of said support and expose said free end of said pin lying within said recess.

16. The method of claim 15 wherein adhesion release means is provided on said distal surface of said base whereby said model or segments thereof can be readily separated from said support.

17. The method of claim 16 wherein multiple tooth positives are provided in said tooth side and at least one dowel pin is provided for each said tooth positive.

18. The method of claim 17 wherein multiple segments of tooth positive moldings and adjacent base portions with their dowel pins affixed thereto are cut from said model and are adapted to be readily removed from and replaced on said support.

19. The method for constructing a combination of a tooth die model and an articulating device comprising providing a model having a tooth side containing at least one tooth positive molding affixed to a proximal surface of a base and having a bite axis, said tooth side and base being oriented generally along said bite axis, affixing at least one dowel pin to said base, said pin having a free end extending outwardly from a distal surface of said base generally along said bite axis, recess form means frictionally mounted on said free end, said form means having an outer end surface portion with shoulder means formed thereon, casting a support of casting material around and encasing said pin and form means whereby as a result of the casting of said support a distal surface thereof and said end surface portion of said form means lie substantially in a common exposed plane, said form means having side surface threads which formed mating threads in said support during casting thereof, engaging said shoulder means by a tool and screwing said form out of said support against the strength of the bond between the cured casting material and said form, said recess becoming exposed upon removal of said form means from said free end and from said support which thereby exposes said free end of said pin lying within said recess, providing an adaptor means for said articulating device having at least one access port therethrough, and mounting said support on said adaptor means with said access port, said recess and said pin end in alignment such that said pin can be forced out of said support by means of a tool inserted thru said access port.

20. The model of claim 19 wherein said adaptor means is cast around a portion of an arm of an articulating device.

21. The method of claim 19 wherein said adaptor means comprises a substantially flat surface upon which said support is cast and wherein said support is further formed during the casting thereof with side access port means which extend from an exterior side surface of said support substantially laterally into a side of said recess for allowing said free end to be readily contacted with force applying tool means for separating the entire die model or segments cut therefrom from said support.

* * * * *